(12) United States Patent
Kansal et al.

(10) Patent No.: US 7,064,198 B2
(45) Date of Patent: Jun. 20, 2006

(54) METHOD FOR PREPARATION OF CEFUROXIME AXETIL

(75) Inventors: Vinod Kumar Kansal, Mandideep (IN); Sunil Gurudatt Bhat, Mandideep (IN); Tanguturi Venkata Marutikumar, Mandideep (IN); Yuvaraj Atmaram Chavan, Mandideep (IN); Ramanathan Sankaran, Mumbai (IN)

(73) Assignee: Lupin Limited, Maharashtra (IN)

(*) Notice: Subject to any disclaimer, the term of this patent is extended or adjusted under 35 U.S.C. 154(b) by 272 days.

(21) Appl. No.: 10/468,584

(22) PCT Filed: Jul. 25, 2001

(86) PCT No.: PCT/IN01/00134

§ 371 (c)(1),
(2), (4) Date: Aug. 20, 2003

(87) PCT Pub. No.: WO03/010170

PCT Pub. Date: Feb. 6, 2003

(65) Prior Publication Data

US 2004/0077850 A1 Apr. 22, 2004

(51) Int. Cl.
*C07D 501/34* (2006.01)
*C07D 501/04* (2006.01)

(52) U.S. Cl. .................................................. 540/222
(58) Field of Classification Search .................. 540/222
See application file for complete search history.

(56) References Cited

U.S. PATENT DOCUMENTS

| 4,267,320 A | 5/1981 | Gregson et al. |
| 5,498,787 A | 3/1996 | Wang et al. |
| 6,833,452 B1 * | 12/2004 | Tyagi et al. ............... 540/222 |
| 2004/0242864 A1 * | 12/2004 | Longoni et al. ............ 540/222 |

FOREIGN PATENT DOCUMENTS

| GB | 2218094 | 11/1989 |
| JP | 05-213968 A | * 8/1993 |

OTHER PUBLICATIONS

Humber et al in "Recent Advances in the Chemistry of the β-Lactam Antibiotics" (1980) pp. 38-45.*
Translation of Japan 05-213968A.*
Yong Seo Cho et al. "Studies on New Oracl Cephalosporin Esters" Korean Journal of Medical Chemistry, vol. 5, No., 1, 1995 pp 60-63.
Hong Woo Lee et al. "Preparation of Ceph-3-Em Esters (Continued)

*Primary Examiner*—Mark L. Berch
(74) *Attorney, Agent, or Firm*—Merchant & Gould P.C.

(57) ABSTRACT

A process for preparation of cefuroxime axetil of formula (I) of at least 96% purity and substantially free of analogous $\Delta^2$-isomer of formula (II) and other impurities. The process comprises

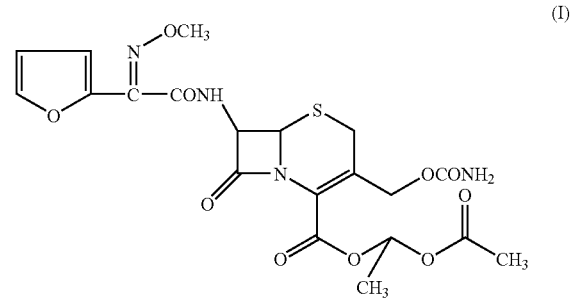

reacting cefuroxime acid of formula (III)

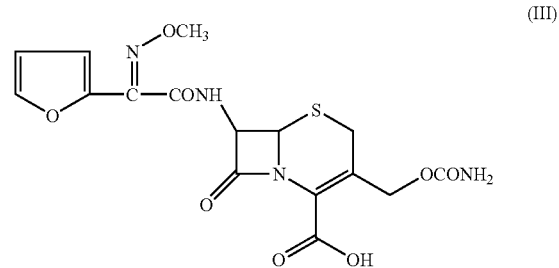

with (R,S)-1-acetoxyethyl bromide of formula (IV),

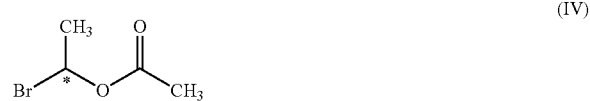

and a Group I or II metal carbonate in the presence of a compound of formula (V), $$M_mH_nP_qO_r \qquad (V)$$

wherein M is Group I or II metal; m is 1, 2, 3; n is 0, 1, 2, or 4; q is 1 or 2; r is 4, 7 or 8; in the presence of a $C_{1-4}$ alcohol and a polar tertiary amide solvent selected from N,N-dimethylacetamide, N,N-dimethylformamide, N,N-dimetheylpropionamide, N,N-diethylacetamide, N,N-diethylformamide and N,N-diethylpropionamide at a temperature ranging from about −30 to +30° C. and subjecting the product thus obtained to a desired step of purification.

23 Claims, No Drawings

OTHER PUBLICATIONS

Unaccompanied by $\Delta^3$ to $\Delta^2$ Isomerization of the Cephalosporin Derivatives" Synthetic Communications, 29 (11), 1873-1887 (1999).

Hon g Woo Lee et al. "An Effective and Convenient Esterification of Cephalosporin Derivatives by using Quartenary Ammonium Salts as Catalysts" Synthetic Communications, 28(23), 4345-4354 (1998).

Thomas P. Demuth, Jr. et al. "Synthesis and Antibacterial Activity of New C-10 Quinolonyl-cephem Esters" The Journal of Antibiotics Feb. 1991, pp 200-209.

G.V. Kaiser, et al. "Chemistry of Cephalosporin Antibiotics. XIX. Transformation of $\Delta^2$-Cephem to $\Delta^3$-Cephem by Oxidation-Reduction at Sulfur" J. Org. Chem., vol. 35, No. 7, 1970.

Shingeto Negi et al. "Studies on the Stability of $\Delta^2$ and $\Delta^3$ Cephem Esters. I. Marked Differences in Stability between $\Delta^2$ and $\Delta^3$ Cephem Prodrug Esters and Application to the Preparation of Key Intermediates for Oral Cephem Synthesis." Chem. Pharm. Bull. 43(11) 1998-2000 (1995).

"The Total Synthesis of Cephalosporin C", JA.C.S. 88, p 852 (1966).

R.B. Morin "Chemistry of Cephalosporin Antibiotics. XV. Transformations of Penicillin Sulfoxide. A Synthesis of Cephalosporin Compounds" J. of the American Chemical Society 91:6 Mar. 12, 1969 pp 1401-1407.

Peter H. Bentley et al. "Phthalidyl Esters of Cephalosporins" Tetrahedron Letters No. 41, pp 3739-3742, 1976. Permagon Press.

Jocelyn G. Millar et al. "Synthesis of Chiral Bis-Homoallylic Epoxides. A New Class of Lepidopteran Sex Attractants." J. Org. Chem. 1986, 51, 4726-4728.

* cited by examiner

METHOD FOR PREPARATION OF CEFUROXIME AXETIL

FIELD OF THE INVENTION

The present invention relates to an improved method for synthesis of cefuroxime axetil of formula (I) in high purity substantially free of the corresponding 2-cephem($\Delta^2$)-ester of formula (II) and other impurities. The compound produced is valuable as a prodrug ester of the corresponding cephalosporin-4-carboxylic acid derivative i. e. cefuroxime, particularly suitable for oral administration in various animal species and in man for treatment of infections caused by gram-positive and gram-negative bacteria.

BACKGROUND OF THE INVENTION

One of the ways to improve the absorption of cephalosporin antibiotics which are poorly absorbed through the digestive tract is to prepare and administer the corresponding ester derivatives at the 4-carboxylic acid position. The esters are then readily and completely hydrolysed in vivo by enzymes present in the body to regenerate the active cephalosporin derivative having the free carboxylic acid at the 4-position.

Among the various ester groups that can be prepared and administered only a selected few are biologically acceptable, in addition to possessing high antibacterial activity and broad antibacterial spectrum. Clinical studies on many such potential "prodrug esters" such as cefcanel daloxate (Kyoto), cefdaloxime pentexil tosilate (Hoechst Marion Roussel) and ceftrazonal bopentil (Roche), to name a few have been discontinued, while ceftizoxime alapivoxil ((Kyoto) in under Phase III clinical studies. The cephalosporin prodrug esters which have been successfully commercialised and marketed include cefcapene pivoxil (Flomox®, Shionogi), cefditoren pivoxil (Spectracef®, Meiji Seika), cefetamet pivoxil (Globocef®, Roche), cefotiam hexetil (Taketiam®, Takeda), cefpodoxime proxetil (Vantin®, Sankyo), cefteram pivoxil (Tomiron®, Toyama) and cefuroxime axetil (Ceftin® and Zinnat®, Glaxo Wellcome).

Typically, such (3,7)-substituted-3-cephem-4-carboxylic acid esters represented by formula (I A) are synthesised by reacting the corresponding (3,7)-substituted-3-cephem-4-carboxylic acid derivative of formula (III A), with the desired haloester compound of formula (IV A) in a suitable organic solvent. The synthesis is summarised in Scheme-I, wherein in compounds of formula (I A), (II A), (III A) and (IV A) the groups $R^1$ and $R^2$ at the 3- and 7-positions of the β-lactam ring are substituents useful in cephalosporin chemistry; $R^3$ is the addendum which forms the ester function and X is halogen.

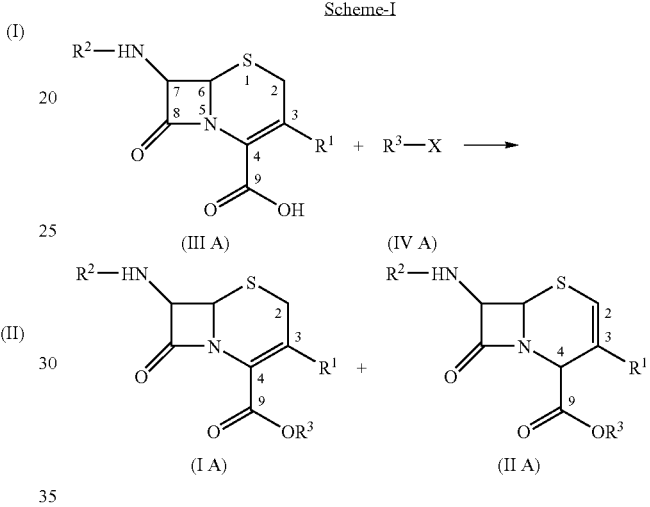

Scheme-I

However, the esterification reaction which essentially involves conversion of a polar acid or salt derivative to a neutral ester product invariably produces the corresponding (3,7)-substituted-2-cephem ($\Delta^2$)-4-carboxylic acid ester derivative of formula (II A) in varying amounts, arising out of isomerisation of the double bond from the 3–4 position to the 2–3 position as well as other unidentified impurities.

It has been suggested [D. H. Bentley, et. al., *Tetrahedron Lett.*, 1976, 41, 3739] that the isomerisation results from the ability of the 4-carboxylate anion of the starting carboxylic acid to abstract a proton from the 2-position of the 3-cephem-4-carboxylic acid ester formed, followed by reprotonation at 4-position to give the said $\Delta^2$-ester. It has also been suggested [R. B. Morin, et. al., *J. Am. Chem. Soc.*, 1969, 91, 1401; R. B. Woodward, et. al., *J. Am. Chem. Soc.*, 1966, 88, 852] that the equilibrium position for isomerisation is largely determined by the size of the ester addendum attached at the 4-carboxylic acid position.

The 2-cephem-4-carboxylic acid esters of formula (II A) are not only unreactive as antibacterial agents but are undesired by-products. Pharmacopoeias of many countries are very stringent about the presence of the 2-cephem analogues in the finished sample of (3,7)-substituted-3-cephem-4-carboxylic acid esters and set limits for the permissible amounts of these isomers. Due to the structural similarity of the 2-cephem and 3-cephem analogues it is very difficult to separate the two isomers by conventional methods, such as chromatography as well as by fractional crystallisation. In addition to this removal of other unidentified impurities formed in the reaction, entails utilisation of tedious purification methods, thus overall resulting in, a) considerable loss in yield, increasing the cost of manufacture and
b) a product of quality not conforming to and not easily amenable for upgradation to pharmacopoeial standards.

Several methods are reported in the prior art for synthesis of cefuroxime axetil of formula (I) and various (3,7)-substituted-3-cephem-4-carboxylic acid esters of formula (I A), with attempts to minimise the unwanted $\Delta^2$-isomers formed in such reactions as well as conversion of the $\Delta^2$-isomer thus formed back to the desired $\Delta^3$-isomer. The prior art methods can be summarised as follows:

(i) U.S. Pat. No. 4,267,320 (Gregson et. al.) describes a method for synthesis of cefuroxime axetil comprising reaction of cefuroxime acid or its alkali metal salts or onium salts with (R,S)-1-acetoxyethyl bromide in an inert organic solvent selected from N,N-dimethylacetamide, N,N-dimethylformamide, dimethyl sulfoxide, acetone, acetonitrile and hexamethylphosphoric triamide at a temperature in the range of −50 to +150° C. The patent mentions that when alkali metal salts, specially potassium salt of cefuroxime acid are employed the reaction can be carried out in a nitrile solvent in the presence of a crown ether. When cefuroxime acid is employed the reaction is carried out in the presence of a weak inorganic base such as sodium carbonate or potassium carbonate, which is added prior to the addition of the haloester. The patent further mentions that the use of potassium carbonate in conjunction with the haloester, specially the bromo or iodo ester is preferred since it helps to minimise the formation of the $\Delta^2$-isomer. Ideally, substantially equivalent amounts of cefuroxime acid and the base is employed.

The U.S. Pat. No. 4,267,320 also describes methods, wherein the said esterification is carried out in the presence of an acid binding agent, which serve to bind hydrogen halide liberated in the reaction, thereby controlling the formation of the $\Delta^2$-isomer. The acid binding agents that are utilised include a tertiary amine base such as triethylamine or N,N-dimethylamine; an inorganic base such as calcium carbonate or sodium bicarbonate and an oxirane compound such as ethylene oxide or propylene oxide.

However, from the examples provided in the above patent the yield of cefuroxime axetil and other (3,7)-substituted-3-cephem-4-carboxylic acid esters obtained is found to be only of about 50%, implying formation of substantial amounts of impurities in the reaction. Indeed, when cefuroxime acid is reacted with (R,S)-1-acetoxyethyl bromide in the presence of 0.55 molar equivalents of sodium carbonate or potassium carbonate in N,N-dimethylacetamide as solvent, as per the process disclosed in this patent, it is found that substantial amounts of the $\Delta^2$-isomer in a proportion ranging from 10–22% is formed, in addition to other unknown impurities. Also, substantial amounts of the starting cefuroxime acid remains unreacted even after 5 hrs of reaction. Isolation of the product generally affords a gummy material, which resists purification even after repeated crystallisations.

Moreover, the use of the acid binding agents mentioned in the above patent, specially tertiary amines and inorganic bases lead to cleavage of the β-lactam ring and also promote the undesired $\Delta^2$-isomerisation, thereby enhancing the level of impurities formed in the reaction.

(ii) (GB Patent No. 2 218 094 describes a method by which the $\Delta^2$-isomers formed during esterification can be converted back to the desired $\Delta^3$-isomers. The method comprises of oxidation of the dihydrothiazine ring in the mixture of $\Delta^2$- and $\Delta^3$-cephalosporin acid esters to the corresponding sulfoxide derivatives with suitable oxidising agents, whereby the $\Delta^2$-isomer gets isomerised to the corresponding $\Delta^3$-isomer during oxidation and the $\Delta^3$-cephalosporin acid ester sulfoxide is isolated. The sulfide group is regenerated back by reduction of the sulfoxide function with suitable reducing agents.

Typically, the oxidation is carried out using m-chloroperbenzoic acid and the reduction achieved by use of an alkali metal halide in presence of acetyl chloride in presence of an inert organic solvent or by use of a phosphorous trihalide.

Although, this method provides the desired $\Delta^3$-isomers in good purity, it cannot be considered as an industrially feasible method since it involves a two step process of oxidation and reduction, isolation of the intermediate products at each stage and necessary purifications, all resulting in considerable loss of the desired product and increase in the cost of manufacture. Moreover, the use of acetyl halide and phosphorous trihalide in the reduction step cannot be applied to cephalosporin derivatives that are sensitive to these reagents.

A similar method has been reported by Kaiser et. al. in *J. Org. Chem.*, 1970, 35, 2430.

(iii) Mobasherry et. al. in *J. Org. Chem.*, 1986, 51, 4723 describe preparation of certain $\Delta^3$-cephalosporin-4-carboxylic acid esters by reaction of the corresponding 3-cephem-4-carboxylic acids (in turn prepared form the corresponding carboxylic acid alkali metal salts) with an haloester in presence of 1.1 eq of sodium carbonate in the presence 1.2–1.5 eq of an alkyl halide and in presence of a solvent comprising of a mixture of N,N-dimethylformamide and dioxane. The authors claim that the method provides of $\Delta^3$-cephalosporin-4-carboxylic acid esters unaccompanied by the corresponding $\Delta^2$-isomer.

However, the method involves an additional step in that the starting 3-cephem-4-carboxylic acid ester derivatives are obtained from the corresponding alkali metal salts prior to reaction. In addition, longer reaction times of about 24 hrs coupled with the fact that it utilises dioxane, a potent carcinogen, not recommended by International Conference on Harmonisation (ICH) on industrial scale renders the method unattractive commercially.

Moreover, on duplication of the method exactly as described in the article it is found that about 3–4% of the corresponding $\Delta^2$-isomer is indeed formed in the reaction in addition to other unidentified impurities. Also, substantial amounts of the starting cephalosporin carboxylic acid is recovered unreacted.

(iv) Shigeto et. al. in *Chem. Pharm. Bull.*, 1995, 43(11), 1998 have carried out the esterification of certain 7-substituted-3-cephem-4-carboxylic acid derivatives with 1-iodoethyl isopropyl carbonate in a solvent system containing a mixture of N,N-dimethylformamide and dioxane in a 3:5 ratio. A conversion to the corresponding 3-cephem-4-carboxylate ester was achieved in only 34%, out of which the $\Delta^2$-isomer amounted to about 8%.

Esterification of 7-formamido-3-(N,N-dimethylcarbamoyloxy)methyl-3-cephem-4-carboxylic acid sodium salt with a suitable haloester in presence of solvents such as N,N-dimethylacetamide and N,N-dimethylformamide, with formation of about 0.8 to 3.0% of the $\Delta^2$-isomer is also reported in the above article by Shigeto et. al. The 7-formamido group was cleaved under acidic conditions to give the corresponding 7-amino derivative contaminated with only about 0.4% of the corresponding $\Delta^2$-isomer. The minimisation of the percentage of $\Delta^2$-isomer is attributed to the relative unstability of 7-amino-2-cephem-4-carboxylic acid esters in acidic conditions, facilitating isomerisation of the 2-cephem intermediate to the 3-cephem derivative.

However, the method does not have a general application, especially for synthesis of commercially valuable cephalosporin derivatives containing hydroxyimino or alkoxyimino substituents in the 7-amino side chain addendum, since these oxyimino functions exhibit a tendency to isomerise from the stable (Z)-configuration to the relatively undesirable (E)-configuration under acidic conditions. This would render separation of the two isomers cumbersome. Moreover, longer reaction times of about 18–20 hrs to effect the isomerisation of the double bond from the 2-position to the 3-position and use of toxic dioxane as solvent impose further limitations on the method.

(v) Demuth et. al. in *J. Antibiotics,* 1991, 44, 200 have utilised the N,N-dimethylformamide-dioxane system in the coupling of 1-iodocephem-4-nitrobenzyl ester with naldixic acid sodium salt and recommend use of dioxane since it reduces the basicity of the quinolone carboxylate and lowers the polarity of the reaction medium.

However, low yields of about 35% and use of toxic dioxane makes the method of little industrial application.

(vi) Wang et. al. in U.S. Pat. No. 5,498,787 claim a method for preparation of certain (3,7)-substituted-3-cephem-4-carboxylic acid prodrug esters, unaccompanied by the analogous 2-cephem esters comprising reaction of the corresponding (3,7)-substituted-3-cephem-4-carboxylic acid alkali metal salts with suitable haloesters in the presence of catalytic amounts of a quarternary ammonium or quarternary phosphonium salt. Among the prodrug esters covered in this patent is cefuroxime axetil.

U.S. Pat. No. 5,498,787 claims that among the quarternary ammonium salts, such salts with acid counter ion, specially tetrabutyl ammonium sulfate ($TBA^+HSO_4^-$) is the most preferred. When the molar ratio of $TBA^+HSO_4^-$/cefuroxime sodium was above 0.40 no $\Delta^2$-isomer was detected, when the said molar ratio was below 0.40 and near about 0.20 the molar ratio of $\Delta^2/\Delta^3$ isomers formed was about 2.0%. When no $TBA^+HSO_4^-$ was added the molar ratio of $\Delta^2/\Delta^3$ isomers formed was about 10.0%. Examples 1 and 2 of this patent illustrate the esterification of cefuroxime sodium in presence of $TBA^+HSO_4^-$ and indicate that the $\Delta^2$-isomer was not detected after 3–12 hours of reaction. The same patent also establishes the superiority of $TBA^+HSO_4^-$ over other salts, specially tetrabutyl ammonium iodide ($TBA^+I^-$) since use of the latter salt resulted in considerable isomerisation of the double bond giving the undesired $\Delta^2$-isomer in predominant amounts.

The present inventors have, however, found that when cefuroxime sodium is reacted with (R,S)-1-acetoxyethyl bromide in the presence of tetrabutylammonium sulfate ($TBA^+HSO_4^-$) as per the method covered in U.S. Pat. No. 5,498,787 the same did not necessarily result in the production of the desired $\Delta^3$ isomer free of the undesired $\Delta^2$ isomer and other impurities. Also, such process had limitations in that the reaction could not be completed at times even at the end of 5.0 hrs. Moreover, the separation of the impurities, from the product proved cumbersome and could not be removed from the product even after successive crystallisations.

(vii) H. W. Lee et. al., *Syntheic Communications,* 1998, 28(23), 4345–4354 have demonstrated a method essentially similar to that claimed in U.S. Pat. No. 5,498,787. The method of preparation of various esters of cefotaxime consists of reacting cefotaxime sodium with the requisite haloester compound in a suitable solvent and in presence of quarternary ammonium salts as phase transfer catalysts. It is claimed that when no quarternary ammonium salts are added the molar ratio (%) of $\Delta^2/\Delta^3$ isomers formed is about 10%. The formation of $\Delta^2$-isomer is minimised when quarternary ammonium salts are added and particularly when the molar ratio of $TBA^+HSO_4^-$/cefotaxime sodium employed is 0.80 the formation of the $\Delta^2$-isomer is completely inhibited.

However, this method requires long hours (~18–24 hrs) and is carried out at higher temperatures (40–45° C.) and as such may not be suitable for cephalosporin derivatives that are sensitive to heat.

(viii) H. W. Lee et. al. in *Synthetic Communications,* 1999, 29(11), 1873–1887 demonstrate a method for preparation of number of (3,7)-substituted-3-cephem-4-carboxylic acid esters comprising reacting the corresponding (3,7)-substituted-3-cephem-4-carboxylic acid derivatives with a base selected form cesium carbonate or cesium bicarbonate either used alone or in combination with potassium carbonate, sodium carbonate, potassium bicarbonate and sodium bicarbonate. The authors established that the formation of $\Delta^2$-isomers could be minimised by utilisation of a solvent combination of N,N-dimethyl formamide and dioxane. The use of the latter mentioned solvent i. e. dioxane was expected to lower polarity of the reaction medium and thereby reduce the basicity of the transient 3-cephem-4-carboxylate anion formed in the reaction and thus preventing the isomerisation of the double bond from the 3–4 position to the 2–3 position.

The formation of the $\Delta^2$-isomer was found to be dependent on the amount of dioxane in the solvent mixture, the more the proportion of dioxane lesser the degree of isomerisation.

However, yields of representative esters obtained by the method are in the range of 45–85%, implying that the reaction is accompanied by formation of substantial amounts of impurities and that the isomerisation is dependent on the nature of the substituent at $3\alpha$-position of the cephalosporin nucleus as well as on the nature of the haloester employed. Moreover, the method utilises dioxane, not desirable for reasons mentioned herein earlier and expensive cesium salts. This method, therefore, also has limited application.

(ix) Y. S. Cho et. al., in *Korean J. Med. Chem.,* 1995, 5(1), 60–63 describe synthesis of several cephalosporin prodrug esters and their efficacy on oral administration. The esters were synthesised by reacting the corresponding cephalosporin-4-carboxylic acid derivative with the respective haloester derivative in presence of cesium carbonate and N,N-dimethylacetamide. The yields of the ester derivatives obtained are in the range of only 25–56%, indicating formation of substantial amounts of impurities in the reaction.

Thus, in summary the prior art methods are associated with one or more of the following shortcomings, which limit their application as an industrially acceptable method for synthesis of various (3,7)-substituted-3-cephem-4-carboxylic acid esters, specially cefuroxime axetil. These are, viz.

a) formation of varying amounts of the undesired 2-($\Delta^2$)-cephem-4-carboxylic acid esters, and other unidentified impurities, specially impurities $X_1$ and $X_2$ mentioned earlier, b) incompleteness of the reaction, resulting in substantial amounts of starting material remaining unreacted, c) employment of tedious/costly techniques for separation of the unwanted $\Delta^2$-isomer, other unidentified impurities and unreacted starting material, d) shortcomings a), b) and c) giving the final product in low yields and of inferior quality, thereby making the methods commercially unviable, e) use of carcinogenic and toxic solvents not acceptable industrially, f) use of additives/catalysts as acid binding agents not efficient enough to prevent the $\Delta^3$- to $\Delta^2$-isomerisation and g) lack of general applicability for synthesis of a variety of (3,7)-substituted-3-cephem-4-carboxylic acid esters.

It is thus the basic object of the present invention to provide for an improved process for manufacture of (3,7)-substituted-3-cephem-4-carboxylic acid esters particularly cefuroxime axetil of formula (I) which would be substantially free of undesired 2-($\Delta^2$)-cephem-4-carboxylic acid esters and any associated impurities.

It is another object of the present invention to provide for an improved synthesis of (3,7)-substituted-3-cephem-4-carboxylic acid esters, particularly cefuroxime axetil of formula (I), which eliminates/minimises the aforesaid shortcomings associated with the prior art methods and provides the object compound(s) in highly pure form, suitable for use in pharmaceuticals.

Another object of the present invention is to provide compounds of formula (I) in high purity i.e. of quality conforming to pharmacopoeial standards.

Yet further object of the present invention is to provide a cost-effective and environmentally benign method for preparation of cefuroxime axetil of formula (I) in high purity utilising cost effective and readily available raw materials and industrially acceptable solvents.

SUMMARY OF THE INVENTION

Thus according to the present invention there is provided an improved method for preparation of (R,S)-1-Acetoxy-ethyl (6R,7R)-3-carbamoyloxymethyl-7-[(Z)-2-(fur-2-yl)-2-methoxyiminoacetamido]ceph-3-em-4-carboxylate i.e. cefuroxime axetil of formula (I), in high purity, substantially free of analogous $\Delta^2$-isomer of formula (II) and other impurities

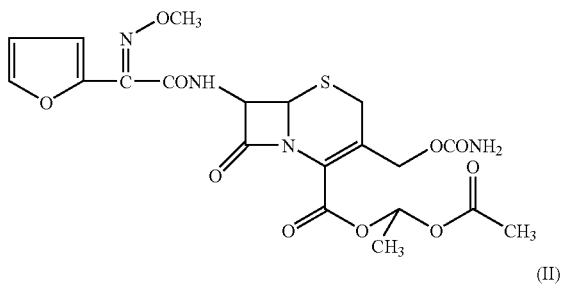

(I)

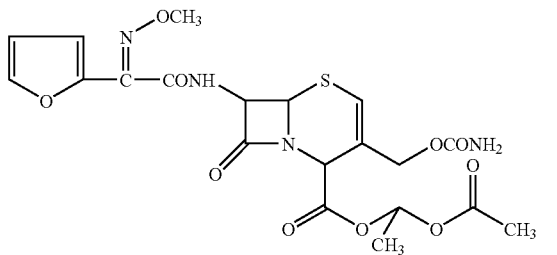

(II)

comprising reacting cefuroxime acid of formula (III)

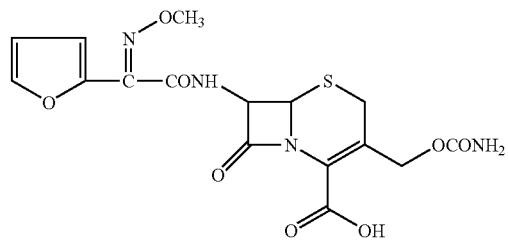

(III)

with (R,S)-1-acetoxyethyl bromide of formula (IV) and a Group I and/or II metal carbonate and in the presence of a Group I and/or II phosphate, hydrogen phosphate or polyphosphate of formula (V),

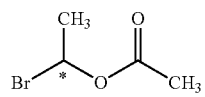

(IV)

$M_m H_n P_q O_r$ (V)

wherein M is a metal selected from Group I or II; m is 1, 2 or 3; n is 0, 1, 2 or 4; q is 1 or 2 and r is 4, 7 or 8 and in presence of a $C_{1-4}$ alcohol in the presence of a polar tertiary amide solvent at a temperature ranging from about −30 to +30° C. and subjecting the product thus obtained to desired step of purification.

DETAILED DESCRIPTION OF THE INVENTION

The embodiments of the present invention is based on the utilisation of the phosphates, hydrogen phosphates or polyphosphates of formula (V) in combination with a $C_{1-4}$ alcohol to eliminate/minimise the formation of unwanted $\Delta^2$-isomer of formula (II) and other unidentified impurities, specially two impurities termed $X_1$ and $X_2$ formed during the course of the reaction of cefuroxime acid of formula (III) and a haloester of formula (IV) in the presence of Group I or II metal carbonates to give cefuroxime axetil of formula (I) in high purity.

The method of preparation of cefuroxime axetil as per the method of the present invention is summarised in Scheme-II.

In a typical method, a solution of cefuroxime acid of formula (III) in a polar tertiary amide solvent is mixed with the Group I or II metal carbonate; Group I or II metal phosphate, hydrogen phosphate or polyphosphate of formula (V); (R,S)-1-acetoxyethyl bromide of formula (IV) and a $C_{1-4}$ alcohol at a temperature ranging from −30 to +30° C. and agitated at a temperature of from about −10 to about +20° C. for about 2 to 8 hrs. At the end of the reaction, the reaction mixture is diluted with water, and the aqueous portion extracted with a suitable organic solvent. Evaporation of the solvent gives the object compound of formula (I), which is further purified by crystallisation.

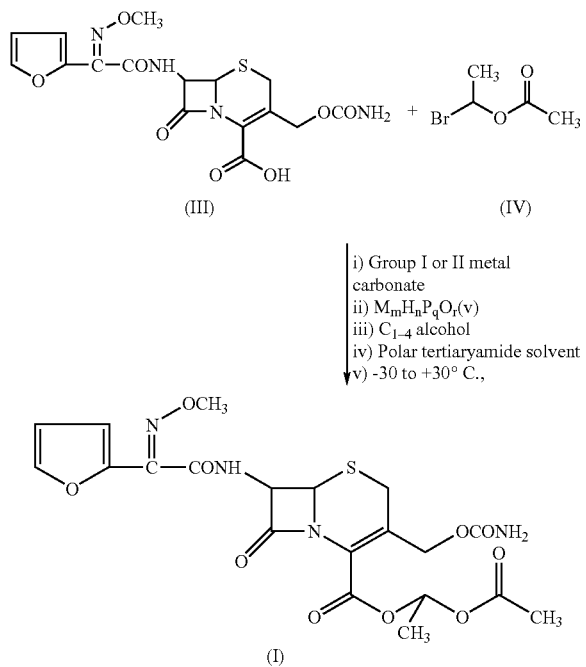

Scheme-II: Method for Preparation of Cefuroxime Axetil as per the Present Invention Preferably, the Group I or II metal phosphate, hydrogen phosphate or polyphosphate may be first added to the solution of cefuroxime acid in the polar solvent, followed by addition of the Group I or II metal carbonate. To the mixture is slowly added (R,S)-1-acetoxyethyl bromide, pre-mixed with the $C_{1-4}$ alcohol and the reaction mixture agitated and worked up as mentioned herein before.

Alternatively, both the Group I or II metal phosphate, hydrogen phosphate or polyphosphate and the Group I or II metal carbonate can be added to the solution of cefuroxime acid in the aprotic solvent, followed by addition of (R,S)-1-acetoxyethyl bromide, pre-mixed with the $C_{1-4}$ alcohol and the reaction performed as described herein earlier.

More preferably, the Group I or II metal carbonate is added first to the solution of cefuroxime acid in the protic solvent, followed by the addition of the Group I or II phosphate, hydrogen phosphate or polyphosphate. To this is then added (R,S)-1-acetoxyethyl bromide, pre-mixed with the $C_{1-4}$ alcohol and the reaction performed as described herein earlier.

The mode of addition of the Group I or II metal carbonate and the phosphate salts as mentioned above does not affect the course of the reaction and all such variations in the mode of addition essentially produce the same result. However, it is most preferred that (R,S)-1-acetoxyethyl bromide be premixed with the $C_{1-4}$ alcohol before addition of the same to the mixture of cefuroxime acid and Group I or II metal carbonate and phosphate salts in the polar solvent.

The polar tertiary amide solvent is selected from N,N-dimethylacetamide, N,N-dimethylformamide, N,N-dimethylpropionamide, N,N-diethylacetamide, N,N-diethylformamide and N,N-diethylpropionamide. Amongst these, N,N-dimethylacetamide and N,N-dimethylformamide are preferred. Furthermore, N,N-dimethylacetamide is preferred over N,N-dimethylformamide since the reaction rate is faster when conducted in the former solvent and takes about 2–4 hrs less time than the reactions conducted in the latter solvent.

The reaction can be carried out at a temperature ranging from about –30 to +30° C. However, when N,N-dimethylacetamide is used as the solvent, taking into consideration the freezing point of the solvent the reaction is preferably carried out at a temperature ranging from about –10 to +30° C.

The rate of reaction is also found to be dependent on the reaction temperature, with higher temperature facilitating faster reaction time. However, at higher temperatures, the isolated product tends to be coloured, which necessiates extra decolourisation steps. This problem is minimised/eliminated when the reaction is performed at lower temperatures and the product obtained is not coloured. Accordingly, most preferably the reaction is carried out a temperature ranging from about –5 to +15° C. in N,N-dimethylacetamide as solvent, which ensures faster reaction rate as well as provides the product of the desired colour and quality.

The alkali and alkaline earth metals from the Group I and II carbonates that can be employed are selected from lithium, sodium, potassium, cesium, magnesium and calcium. Conveniently, substantially equivalent amounts of the alkali or alkaline earth metal carbonate and cefuroxime acid is employed, e.g. about 0.5 moles of the diacidic base per mole of cefuroxime. The carbonate salts can also be employed in excess of equivalent molar ratio and can be employed in a ratio from about 0.55 to 1.00 per mole of cefuroxime acid. Preferably, the molar ratio is from about 0.55 to 0.90.

The Group I alkali metal carbonates are preferred over the Group II alkaline earth metal carbonates and sodium carbonate is the most preferred metal carbonate.

The Group I or II metal phosphates, hydrogen phosphates or polyphosphates of formula (V) that can be employed in the method include the respective alkali metal salts of lithium, sodium, potassium and cesium as well as the respective alkaline earth metal salts of magnesium and calcium. These phosphate salts also include the orthophosphates and metaphosphates and are cheap and readily available.

The salts of formula (V) can be employed in molar proportions of about 0.10 to about 0.80 equivalents per mole of cefuroxime acid. The lower and upper limit are equally effective in significantly minimising/inhibiting the formation of the $\Delta^2$-isomer. When the concentration of compound of formula (V) is below 0.10 molar equivalents, the formation of the $\Delta^2$-isomer is found to be more, while use of compound (V) in excess of 0.80 molar equivalents is found to slow down the reaction rate. A preferred range is, however, from about 0.10 to 0.40 molar equivalents.

The Group I or II metal in such phosphates, hydrogen phosphates and polyphosphates are selected from lithium, sodium, potassium cesium, magnesium and calcium. Amongst these,
i) the more preferred tribasic phosphates are sodium phosphate ($Na_3PO_4$), potassium phosphate ($K_3PO_4$), lithium phosphate ($Li_3PO_4$), magnesium phosphate [$Mg_3(PO_4)_2$] and calcium phosphate [$Ca_3(PO_4)_2$] and all their hydrates thereof.
ii) the more preferred dibasic hydrogen phosphates are lithium dihydrogen phosphate ($LiH_2PO_4$), sodium dihydrogen phosphate ($NaH_2PO_4$), potassium dihydrogen phosphate ($KH_2PO_4$), magnesium hydrogen phosphate ($MgHPO_4$) and all their hydrates thereof.

iii) the more preferred monobasic hydrogen phosphates include sodium dihydrogen phosphate ($Na_2HPO_4$), potassium dihydrogen phosphate ($K_2HPO_4$), magnesium biophosphate ($MgH_4PO_8$) and calcium biophosphate ($CaH_4P_2O_8$) and all their hydrates thereof.

iv) the more preferred polyphosphates include sodium metaphosphate ($Na_4P_2O_7$), sodium polymetaphosphate ($NaPO_3)_x$, potassium pyrophosphate ($K_4P_2O_7$), calcium pyrophosphate ($Ca_2P_2O_7$) and hydroxylapatite [$3Ca_3(PO_4)_2 \cdot Ca(OH)_2$] and all their hydrates thereof.

The alkali metal and alkaline earth metal phosphates, hydrogen phosphates and polyphosphates mentioned hereinabove can be employed singularly or in combination, preferably singularly.

Of the Group I and Group II metal phosphates, hydrogen phosphates and polyphosphates the Group I alkali metal salts are preferred.

Of the Group I alkali metal phosphates, hydrogen phosphates and polyphosphates the alkali metal hydrogen phosphates are more preferred.

Of the alkali metal hydrogen phosphates, the alkali metal dihydrogen phosphates such as sodium dihydrogen phosphate ($Na_2HPO_4$) and potassium dihydrogen phosphate ($K_2HPO_4$) are further more preferred.

Of the alkali metals, sodium is the most preferred and the most preferred alkali metal dihydrogen phosphate of the present invention is sodium dihydrogen phosphate ($Na_2HPO_4$).

The $C_{1-4}$ alcohol employed in the invention is selected from methanol, ethanol, n-propanol, iso-propanol, n-butanol, iso-butanol and tert-butanol. These alcohols completely eliminate the formation of the unidentified impurities, viz. impurities $X_1$ and $X_2$ formed in the reaction Typically, the alcohol is mixed with the haloester, viz. (R,S)-1-acetoxyethyl bromide prior to esterification, at a temperature ranging from about 15 to 40° C. The alcohol can be employed in 0.03 to 0.15 molar equivalents per mole of cefuroxime acid. The lower limit completely inhibits the formation of the abovementioned unidentified impurities, $X_1$ and $X_2$. Employment of the alcohol in proportions up to and above the upper limit not only completely inhibits the formation of the impurities, $X_1$ and $X_2$, but does not create any adverse effect in the reaction, and more importantly does not lead to formation of additional impurities. However, about 0.5 to 1.0% of total impurities are formed when the $C_{1-4}$ alcohol is used below 0.03 molar equivalents per mole of cefuroxime acid. Preferably, the alcohol is employed from about 0.04 to 0.11 molar equivalents per mole of cefuroxime acid. All the $C_{1-4}$ alcohols that are employed in the method are equally effective. However, methanol is the most preferred.

The effect of utilising combination of the Group I or II metal phosphates, hydrogen phosphates or polyphosphates and the $C_{1-4}$ alcohol in elimination/minimisation of the $\Delta^2$-isomer of formula (II) and the unidentified impurities $X_1$ and $X_2$ and any other impurity formed during the esterification of cefuroxime acid of formula (III) with (R,S)-1-acetoxyethyl bromide of formula (IV) and a Group I or II metal carbonate can be seen from the following non-illustrative results summarised in Table-I.

The (R,S)-1-acetoxyethyl bromide of formula (IV) used for the esterification is employed in a ratio of about 1.5–2.5 molar equivalents per mole of cefuroxime acid, preferably in a ratio of about 1.8–2.0 molar equivalents.

The haloester of formula (IV) is prepared by methods known in the art.

Since the halo esters employed have one chiral centre and are obtained and utilised for the alkylation reaction as a mixture of (R)- and (S)-isomers, the cefuroxime axetil of formula (I) is obtained as a mixture of two diastereomers. Commercially cefuroxime

TABLE I

The reaction of Cefuroxime acid (III) with (R, S)-1-acetoxyethyl bromide** (IV) and Group I or II in metal carbonates in the presence of Group I or metal phosphates, hydrogen phosphates or polyphosphates of fomula (V) and a $C_{1-4}$ alcohol in N,N-dimethylacetamide as solvent to give Cefuroxine axetil ($\Delta^3$-isomer, 1).

| Sr. No. | Group I/II metal Carbonate (M eq of (III)) | Compound (V) (M eq of (III)) | $C_{1-4}$ alcohol (M eq of (III)) | Reaction Temperature (° C.) | Reaction Time (hrs.) | % unreacted Cefuroxime acid (III) | % $\Delta^3$-isomer (I) | % $\Delta^2$-isomer (II) | % impurity $X_1$ | % impurity $X_2$ | Yield of Isolated (I) (% molar) |
|---|---|---|---|---|---|---|---|---|---|---|---|
| 01 | $K_2CO_3$ (0.75) | — | — | 0 | 5.00 | 10.63 | 81.87 | 2.88 | 2.24 | 2.58 | 75.00 (sticky solid) |
| 02 | $K_2CO_3$ (0.50) | — | — | 0–5 | 4.50 | 8.09 | 80.27 | 4.49 | 4.59 | 1.84 | 62.50 (sticky solid) |
| 03 | $Na_2CO_3$ (0.80) | $Na_2HPO_4$ (0.10) | — | 0–5 | 3.00 | 3.55 | 85.18 | 1.50 | 4.06 | 4.00 | 87.50 |
| 04 | $Na_2CO_3$ (0.55) | — | $CH_3OH$ (0.20) | 0–5 | 4.00 | 8.77 | 78.76 | 9.80 | — | — | 58.30 |
| 05 | $Na_2CO_3$ (0.70) | — | $CH_3OH$ (0.20) | 0 | 10.0 | 7.10 | 83.70 | 4.90 | — | — | 81.37 |
| 06 | $K_2CO_3$ (0.69) | $K_2HPO_4$ (0.10) | $CH_3OH$ (0.20) | 0 | 4.00 | 2.00 | 93.90 | 1.30 | — | — | 87.50 |
| 07 | $K_2CO_3$ (0.68) | $K_2HPO_4$ (0.4-) | $CH_3OH$ (0.75) | 0 | 4.00 | 2.90 | 94.15 | 1.10 | — | — | 88.10 |
| 08 | $Na_2CO_3$ (0.80) | $NaH_2PO_4$ (0.15) | $C_2H_5OH$ (0.80) | 0 | 5.50 | 2.50 | 93.50 | 0.90 | — | — | 87.90 |
| 09 | $Na_2CO_3$ (0.80) | $NaH_2PO_4$ (0.15) | $CH_3OH$ (0.62) | 0 | 5.00 | 2.80 | 92.00 | 1.10 | — | — | 87.00 |

TABLE I-continued

The reaction of Cefuroxime acid (III) with (R, S)-1-acetoxyethyl bromide** (IV) and Group I or II in metal carbonates in the presence of Group I or metal phosphates, hydrogen phosphates or polyphosphates of fomula (V) and a $C_{1-4}$ alcohol in N,N-dimethylacetamide as solvent to give Cefuroxine axetil ($\Delta^3$-isomer, 1).

| Sr. No. | Group I/II metal Carbonate (M eq of (III)) | Compound (V) (M eq of (III)) | $C_{1-4}$ alcohol (M eq of (III)) | Reaction Temperature (° C.) | Reaction Time (hrs.) | % unreacted Cefuroxime acid (III) | % $\Delta^3$-isomer (I) | % $\Delta^2$-isomer (II) | % impurity $X_1$ | % impurity $X_2$ | Yield of Isolated (I) (% molar) |
|---|---|---|---|---|---|---|---|---|---|---|---|
| 10 | $Na_2CO_3$ (0.75) | $Ca(H_2PO_4)_2$ (0.15) | $CH_3OH$ (0.62) | 0 | 6.00 | 8.20 | 86.90 | 0.83 | — | — | −81.30 |
| 11 | $Na_2CO_3$ (0.80) | $Na_4P_2O_7$ (0.15) | $CH_3OH$ (0.4) | 0–5 | 5.00 | 3.90 | 91.60 | 1.00 | — | — | 86.10 |
| 12 | $Na_2CO_3$ (0.80) | $Na_4P_2O_7$ (0.40) | $CH_3OH$ (0.62) | 0–5 | 4.50 | 4.60 | 91.30 | 0.96 | — | — | 86.00 |
| 13 | $Na_2CO_3$ (0.80) | $Na_3PO_4$ (0.15) | $CH_3OH$ (0.62) | 0–5 | 3.50 | 5.00 | 90.70 | 1.50 | — | — | 85.50 |
| 14 | $Na_2CO_3$ (0.80) | $Na_2HPO_4$ (0.80) | $CH_3OH$ (0.41) | 0–5 | 7.00 | 1.20 | 94.60 | 1.00 | — | — | 88.10 |
| 15 | $Na_2CO_3$ (0.72) | $Na_2HPO_4$ (0.60) | $CH_3OH$ (0.41) | 0–5 | 7.00 | 1.10 | 94.30 | 1.12 | — | — | 87.90 |
| 16 | $Na_2CO_3$ (0.80) | $Na_2HPO_4$ (0.40) | $CH_3OH$ (0.40) | 0–5 | 6.30 | 1.10 | 94.00 | 1.20 | — | — | 87.50 |
| 17 | $Na_2CO_3$ (0.77) | $Na_2HPO_4$ (0.12) | $CH_3OH$ (0.40) | 0–5 | 6.00 | 1.29 | 93.80 | 1.41 | — | — | 87.10 |
| 18 | $Na_2CO_3$ (0.80) | $Na_2HPO_4$ (0.10) | $CH_3OH$ (0.40) | 0–5 | 1.45 | 1.92 | 93.20 | 1.58 | — | — | 86.90 |
| 19 | $Na_2CO_3$ (0.80) | $Na_2HPO_4$ (0.40) | $CH_3OH$ (0.40) | 0–5 | 4.30 | 1.66 | 93.93 | 1.20 | — | — | 87.80 |
| 20 | $Na_2CO_3$ (0.80) | $NaH_2PO_4$ (0.15) | $C_2H_5OH$ (0.80) | 0–5 | 5.50 | 2.50 | 93.50 | 1.00 | — | — | 87.80 |
| 21 | $Na_2CO_3$ (0.8) | $Na_4P_2O_7$ (0.40) | Iso-butanol (0.50) | 0–5 | 4.50 | 4.60 | 91.30 | 0.96 | — | — | 86.10 |
| 22 | $Na_2CO_3$ (0.75) | $CaH_2PO_4$ (0.15) | n-butanol (0.87) | 0–5 | 6.00 | 8.20 | 86.90 | 0.83 | — | — | 85.41 |
| 23 | $K_2CO_3$ (0.68) | $K_2HPO_4$ (0.40) | $CH_3OH$ (0.75) | 0 | 4.00 | 2.90 | 94.15 | 1.10 | — | — | 88.80 |
| 24 | $Na_2CO_3$ (0.80) | $NaH_2PO_4$ (0.15) | $CH_3OH$ (0.62) | 0 | 6.00 | 3.90 | 93.79 | 0.83 | — | — | 88.68 |
| 25 | $Na_2CO_3$ (0.80) | $Na_4P_2O_7$ (0.15) | $CH_3OH$ (0.40) | 0–5 | 5.00 | 3.90 | 93.60 | 1.00 | — | — | 88.40 |
| 26 | $Na_2CO_3$ (0.80) | $Na_2HPO_4$ (0.10) | $CH_3OH$ (0.20) | 0–5 | 5.00 | 4.00 | 91.94 | 1.40 | 0.63 | 0.63 | 87.68 |
| 27 | $Na_2CO_3$ (0.80) | $Na_2HPO_4$ (0.10) | $CH_3OH$ (0.10) | 0–5 | 5.00 | 3.80 | 91.30 | 1.02 | 1.11 | 1.12 | 86.78 |
| 28 | $Na_2CO_3$ (0.80) | $TBA^+HSO_4^-$ (0.20) | $CH_3OH$ (0.20) | R.T. | 7.50 | 4.00 | 88.30 | 4.30 | — | — | 70.83 |
| 29 | $Na_2CO_3$ (0.80) | $TBA^+HSO_4^-$ (0.40) | $CH_3OH$ (0.20) | R.T. | 8.50 | 6.60 | 86.90 | 3.50 | — | — | 66.66 |
| 30 | $Na_2CO_3$ (0.80) | $TBA^+HSO_4^-$ (0.10) | $CH_3OH$ (0.20) | R.T. | 8.0 | 3.10 | 86.40 | 5.10 | — | — | 62.50 |

(*) HPLC Conditions: NOVAPAK C-18 (3.9 × 150 mm) column; Mobile Phase-0.02 M $(NH_4)H_2PO_4$ - Methanol (62:38); Wavelength-278 nm; Flow 1.5 ml/min; Attenuation-7; Chart Speed-0.5 mm/min; Retention Times (mins): (III)-0.98; (I)-diastereomer B 4.50; (I)-diastereomer A 5.30; (II) 6.20; $X_1$ 16–20; $X_2$ 46–60
(**) In all reactions 2.0 M eq. of (R, S)-1-acetoxy ethyl bromide (IV) per mole of Cefuroxime acid (III) was used.

axetil and other prodrug esters such as cefpodoxime proxetil and cefotiam hexetil are sold as a diastereomeric mixture.

After the reaction, the product is isolated by first diluting with water and extracted into a water immiscible organic solvent. Solvents in which the prodrug esters are easily soluble are preferred and these include dichloroethane, dichloromethane, ethyl acetate and methyl isobutyl ketone. The product can be isolated by evaporation of the solvent.

The $\Delta^2$-isomer formed in the reaction can be easily removed by crystallisation of the solid thus obtained either from the same solvent or from a mixture of solvents selected from dichloroethane, dichloromethane, ethyl acetate, methyl isobutyl ketone, hexane, toluene, xylene, diisopropyl ether and tertiary butylmethyl ether. A mixture of ethyl acetate with toluene or xylene is the most preferred.

Cefuroxime axetil obtained by the present method is a crystalline material, the X-ray (powder) diffraction of which matches exactly with the product obtained by the process described by Gregson et. al. in U.S. Pat. No. 4,267,320.

Cefuroxime axetil obtained in high yields of about 85–92% contain the undesired $\Delta^2$-isomer, within the pharmacopoeially acceptable limits. Typically, the product after crystallisation contains only <0.10% of the $\Delta^2$-isomer, a value very well below the prescribed pharmacopoeial limits.

The embodiments of the invention can be best understood from the following non-limiting examples.

EXAMPLE-1

Preparation of (R,S-1-Acetoxyethyl-3-carbamoyloxymethyl-7-[(Z)-2-(fur-2-yl)-2-methoxyiminoacetamido]ceph-3-em-4-carboxylate (Cefuroxime axetil, I): Without use of Group I/II metal phosphate and $C_{1-4}$ alcohol (R,S)-1-Acetoxyethyl bromide (1.6 gms; 0.0094 moles) was added to a mixture of cefuroxime acid (2 gms; 0.0047 moles) and potassium carbonate (0.326 gms; 0.00235 moles) in N,N-dimethylacetamide (10 ml) at 5° C. and stirred at 0 to 20° C. for 180 minutes. Ethyl acetate was added to the reaction mixture, followed by 3% aqueous sodium bicarbonate solution (15 ml). The organic layer containing the title product, $\Delta^2$ isomer (8.51%) and unidentified impurities ($X_1$—1.86% and $X_2$—3.54%) was separated and washed with 10% aqueous NaCl solution. The organic solvent was evaporated off under vacuum to give 1.08 gms (44.90%) of the title compound as a gummy solid.

HPLC analysis: Purity (compound I)—89.11%; Impurities: $\Delta^2$ isomer (II)—8.51%, $X_1$—1.86% and $X_2$—3.54%

EXAMPLE-2

Preparation of (R,S-1-Acetoxyethyl-3-carbamoyloxymethyl-7-[(Z)-2-(fur-2-yl)-2-methoxyiminoacetamido]ceph-3-em-4-carboxylate (Cefuroxime axetil, I): in presence of disodium hydrogen phosphate and methanol (R,S)-1-Acetoxyethyl bromide (3.94 gms; 0.0235 moles) pre-mixed with methanol (0.15 gms; 0.0047 moles) was added to a stirred mixture of cefuroxime acid (5 gms; 0.0118 moles), sodium carbonate (0.94 gms; 0.0088 moles) and disodium hydrogen phosphate (1.0 gms; 0.007 moles) in N,N-dimethylacetamide (20 ml) at 0° C. The mixture was stirred at 0 to 20° C. for 180 minutes. Ethyl acetate was added to the reaction mixture, followed by 3% aqueous sodium bicarbonate solution (25 ml). The organic layer was separated and washed with 10% aqueous sodium chloride solution. The organic extract was stirred with activated charcoal (0.5 gms) for 30 minutes and filtered through a celite bed. The organic layer was evaporated under vacuum and the solid obtained crystallised from a mixture of ethyl acetate/xylene. The crystallised material was filtered and dried at 40 to 45° C. under vacuum to give 5.26 gms (87.5%) of the title compound.

HPLC analysis: Purity (compound I) ≧96.00%; Impurities: $\Delta^2$ isomer (II)—<0.10%, $X_1$ and $X_2$—NIL $[\alpha]_D$ (1% Dioxan): +37°

IR (KBr): 3500, 3417, 1780, 1749 $cm^{-1}$ $^1$H NMR ($d^6$-DMSO; δ): 1.46 (bd, 3H, $CH_3$), 2.04 (s, $CH_3CO$), 2.05 (s, $CH_3CO$), 3.58 (q, $CH_2S$), 3.88 (s, $CH_3O$), 4.69 (dd, $CH_2O$; J=4 Hz), 4.78 (dd, $CH_2O$, J=1 Hz), 5.075 (t, 1H, 6H), 5.85 (m, 1H, 7H), 6.6–6.7 (m, 2H), 6.89 (q, $CH_3$—CH), 7.01 (q, $CH_3CH$), 7.82 (d, 1h) and 9.60 (dd, 1H, CONH).

EXAMPLE-3

Preparation of (R,S-1-Acetoxyethyl-3-carbamoyloxymethyl-7-[(Z)-2-(fur-2-yl)-2-methoxyiminoacetamido]ceph-3-em-4-carboxylate (Cefuroxime axetil, I): in presence of sodium dihydrogen phosphate and ethanol (R,S)-1-Acetoxyethyl bromide (3.94 gms; 0.0235 moles) pre-mixed with ethanol (0.434 gms; 0.0090 moles) was added to a stirred mixture of cefuroxime acid (5 gms; 0.0118 moles), sodium carbonate (1.0 gms; 0.0090 moles) and sodium dihydrogen phosphate (0.21 gms; 0.0017 moles) in N,N-dimethylacetamide (20 ml) at 0–5° C. The mixture was stirred at 0 to 20° C. for 180 minutes. Ethyl acetate was added to the reaction mixture, followed by 3% aqueous sodium bicarbonate solution (25 ml). The organic layer was separated and washed with 10% aqueous sodium chloride solution. The organic extract was stirred with activated charcoal (0.5 gms) for 30 minutes and filtered through a celite bed. The organic layer was evaporated under vacuum and the solid obtained crystallised from a mixture of ethyl acetate/xylene. The crystallised material was filtered and dried at 40 to 45° C. under vacuum to give 5.28 gms (87.8%) of the title compound.

HPLC analysis: Purity (compound I) ≧96.00%; Impurities: $\Delta^2$ isomer (II) <0.10%, $X_1$ and $X_2$—NIL

EXAMPLE-4

Preparation of (R,S-1-Acetoxyethyl-3-carbamoyloxymethyl-7-[(Z)-2-(fur-2-yl)-2-methoxyiminoacetamido]ceph-3-em-4-carboxylate (Cefuroxime axetil, I): in presence of calcium monophosphate and n-butanoll (R,S)-1-Acetoxyethyl bromide (3.94 gms; 0.0235 moles) pre-mixed with n-butanol (0.87 gms; 0.0118 moles) was added to a stirred mixture of cefuroxime acid (5 gms; 0.0118 moles), sodium carbonate (0.93 gms; 0.0880 moles) and calcium monophosphate (0.41 gms; 0.00177 moles) in N,N-dimethylacetamide (20 ml) at 0–5° C. The mixture was stirred at 0 to 20° C. for 180 minutes. Ethyl acetate was added to the reaction mixture, followed by 3% aqueous sodium bicarbonate solution (25 ml). The organic layer was separated and washed with 10% aqueous sodium chloride solution. The organic extract was stirred with activated charcoal (0.5 gms) for 30 minutes and filtered through a celite bed. The organic layer was evaporated under vacuum and the solid obtained crystallised from a mixture of ethyl acetate/xylene. The crystallised material was filtered and dried at 40 to 45° C. under vacuum to give 5.29 gms (87.96%) of the title compound.

HPLC analysis: Purity (compound I) ≧96.00%; Impurities: $\Delta^2$ isomer (II) <0.10%, $X_1$ and $X_2$—NIL

EXAMPLE-5

Preparation of (R,S-1-Acetoxyethyl-3-carbamoyloxymethyl-7-[(Z)-2-(fur-2-yl)-2-methoxyiminoacetamido]ceph-3-em-4-carboxylate (Cefuroxime axetil, I): in presence of dipotassium hydrogenphosphate and iso-propanol (R,S)-1-Acetoxyethyl bromide (3.94 gms; 0.0235 moles) pre-mixed with iso-propanol (0.70 gms; 0.0118 moles) was added to a stirred mixture of cefuroxime acid (5 gms; 0.0118 moles), potassium carbonate (1.11 gms; 0.0080 moles) and dipotassiumihydrogen phosphate (0.82 gms; 0.0047 moles) in N,N-dimethylacetamide (20 ml) at 0–5° C. The mixture was stirred at 0 to 20° C. for 180 minutes. Ethyl acetate was added to the reaction mixture followed by 3% aqueous sodium bicarbonate solution (25 ml). The organic layer was separated and washed with 10% aqueous sodium chloride solution. The organic extract was stirred with activated charcoal (0.5 gms) for 30 minutes and filtered through a celite bed. The organic layer was evaporated under vacuum and the solid obtained crystallised from a mixture of ethyl acetate/xylene. The crystallised material was filtered and dried at 40 to 45° C. under vacuum to give 5.28 gms (87.8%) of the title compound.

HPLC analysis: Purity (compound I) ≧96.00%; Impurities: $\Delta^2$ isomer (II) <0.10%, $X_1$ and $X_2$—NIL

EXAMPLE-6

Preparation of (R,S-1-Acetoxyethyl-3-carbamoyloxymethyl-7-[(Z)-2-(fur-2-yl)-2-methoxyiminoacetamido]ceph-3-em-4-carboxylate (Cefuroxime axetil, I): in presence of sodium pyrophosphate and iso-butanol (R,S)-1-Acetoxyethyl bromide (3.94 gms; 0.0235 moles) pre-mixed with iso-butanol (0.87 gms; 0.0118 moles) was added to a stirred mixture of cefuroxime acid (5 gms; (0.0118 moles), sodium carbonate (1.00 gms; 0.0090 moles) and sodium pyrophosphate (1.25 gms; 0.0047 moles) in N,N-dimethylacetamide (20 ml) at 0–5° C. The mixture was stirred at 0 to 20° C. for 180 minutes. Ethyl acetate was added to the reaction mixture, followed by 3% aqueous sodium bicarbonate solution (25 ml). The organic layer was separated and washed with 10% aqueous sodium chloride solution. The organic extract was stirred with activated charcoal (0.5 gms) for 30 minutes and filtered through a celite bed. The organic layer was evaporated under vacuum and the solid obtained crystallised from a mixture of ethyl acetate/xylene. The crystallised material was filtered and dried at 40 to 45° C. under vacuum to give 5.28 gms (87.8%) of the title compound.

HPLC analysis: Purity (compound I) ≧96.00%; Impurities $\Delta^2$ isomer (II) <0.10%, $X_1$ and $X_2$—NIL

What is claimed is:

1. A process for preparation of cefuroxime axetil of formula (I) of at least 96% purity,

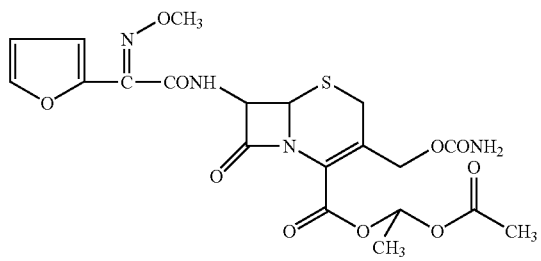

comprising
(a) reacting cefuroxime acid of formula (III)

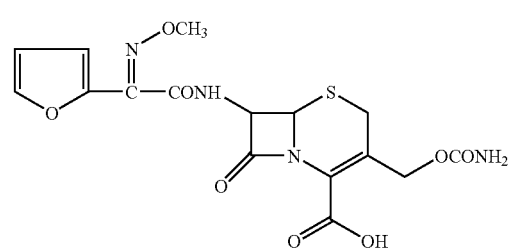

with (R,S)-1-acetoxyethyl bromide of formula (IV),

and a Group I or II metal carbonate in the presence of a compound of formula (V),

$$M_mH_nP_qO_r \quad (V)$$

wherein M is Group I or II metal; m is 1, 2 or 3; n is 0, 1, 2 or 4; q is 1 or 2 and r is 4, 7 or 8;
in the presence of a $C_{1-4}$ alcohol and solvent, the solvent comprising N,N-dimethylacetamide, N,N-dimethylformamide, N,N-dimetheylpropionamide, N,N-diethylacetamide, N,N-diethylformamide, or N,N-diethylpropionamide, at a temperature ranging from about −30 to +30° C. and
(b) purifying the product of step (a).

2. A process as claimed in claim 1, wherein said step of purification comprises evaporation of the solvent from the reaction product followed by crystallisation of a solid residue.

3. A process as claimed in claim 1, wherein the polar tertiary amide solvent comprises N,N-dimethylacetamide.

4. A process as claimed in claim 1, wherein the metal in the Group I or II metal carbonate is selected from lithium, sodium, potassium, cesium, magnesium, or calcium.

5. A process as claimed in claim 1, wherein said metal carbonate comprises Group I alkali metal carbonate.

6. A process as claimed in claim 1, wherein the compound of formula (V) comprises Group I alkali metal salt comprises metal phosphate, hydrogen phosphate and polyphosphate, or a mixture thereof.

7. A process as claimed in claim 1, wherein Group I or II metal in compound of formula (V) comprises lithium, sodium, potassium, cesium, magnesium, or calcium.

8. A process as claimed in claim 1, wherein the molar ratio of Group I or II metal carbonate is 0.55 to 1.0 mole equivalent per mole of compound of formula (III).

9. A process as claimed in claim 1, wherein the molar ratio of Group I or II metal carbonate is 0.55 to 0.70 mole equivalent per mole of compound of formula (III).

10. A process as claimed in claim 1, wherein the molar ratio of compound of formula (IV) is 1.5 to 2.5 mole equivalent per mole of compound of formula (III).

11. A process as claimed in claim 10, wherein the molar ratio of compound of formula (IV) is 1.8 to 2.0 mole equivalent per mole of compound of formula (III).

12. A process as claimed in claim 1, wherein the molar ratio of compound of formula (V) is 0.10 to 0.80 mole equivalent per mole of compound of formula (III).

13. A process as claimed in claim 12, wherein the molar ratio of compound of formula (V) is 0.10 to 0.40 mole equivalent per mole of compound of formula (III).

14. A process as claimed in claim 1, wherein the $C_{1-4}$ alcohol comprises methanol, ethanol, n-propanol, iso-propanol, n-butanol, iso-butanol or tert-butanol.

15. A process as claimed in claim 1, wherein the $C_{1-4}$ alcohol is employed in about 0.03 to 0.15 moles per mole of compound of formula (III).

16. A process as claimed in claim 1, wherein the temperature is from about −10 to +20° C.

17. A process as claimed in claim 16, wherein the $C_{1-4}$ alcohol is employed in about 0.04 to 0.11 moles per mole of compound of formula (III).

18. A process as claimed in claim 2, wherein the solvent for crystallisation comprises dichloroethane, dichloromethane, ethyl acetate, methyl isobutyl ketone, or a mixture of any of these solvents with hexane, toluene, xylene, diisopropyl ether and tertiarybutylmethyl ether.

19. A process as claimed in claim 1, wherein compounds of formula (I) are obtained in at least 96% purity and the corresponding $\Delta^2$ impurity of formula (II)

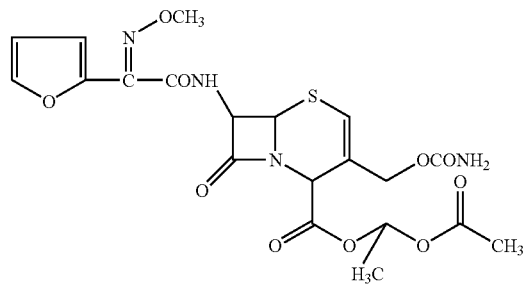

is less than 0.1% and impurities $X_1$ and $X_2$ are absent.

20. A process as claimed in claim 5, wherein Group I alkali metal carbonate comprises sodium carbonate.

21. A process as claimed in claim 15, wherein the $C_{1-4}$ alcohol comprises methanol.

22. A process as claimed in claim 4, wherein the metal comprises sodium or potassium.

23. A process as claimed in claim 7, wherein the metal comprises sodium.

* * * * *